United States Patent [19]

Rutledge

[11] 4,438,037

[45] Mar. 20, 1984

[54] OXIDATION OF AROMATIC COMPOUNDS TO QUINONES BY USE OF SODIUM HYPOCHLORITE

[75] Inventor: Thomas F. Rutledge, Avalon, N.J.

[73] Assignee: ICI Americas Inc., Wilmington, Del.

[21] Appl. No.: 412,140

[22] Filed: Aug. 27, 1982

[51] Int. Cl.$^3$ .................. C07C 45/28; C07C 50/18
[52] U.S. Cl. .................................. 260/385; 260/369
[58] Field of Search .............................. 260/385, 369

[56] References Cited

U.S. PATENT DOCUMENTS 2,120,678  6/1938  Parsons et al. .................... 162/87
2,821,534  1/1958  Alexander .......................... 260/385
3,291,825  12/1966  Greco ................................ 260/385

OTHER PUBLICATIONS

*Chemical Abstracts*, vol. 82, #111821f, 1974, "Reaction of Chlorine Dioxide and Sodium Chlorite with Some Organic Compounds", Paluch.

*FUEL*, vol. 54, 1975, pp. 273-275, Mayo, "Application of Sodium Hypochlorite Oxidations to the Structure of Coal".

*Kirk-Othimer, Encyclopedia of Chemical Technology*, vol. 3, pp. 554-561, "Bleaching Agents".

*Primary Examiner*—Natalie Trousof
*Assistant Examiner*—Raymond Covington
*Attorney, Agent, or Firm*—H. J. Lammers

[57] ABSTRACT

Anthracenes may be converted to their corresponding quinones by dissolving the anthracenes in an inert solvent and oxidizing the dissolved anthracenes with sodium hypochlorite as an oxidating agent where the reaction mixture has a pH in the range of 4.5 to 8.0.

7 Claims, No Drawings

OXIDATION OF AROMATIC COMPOUNDS TO QUINONES BY USE OF SODIUM HYPOCHLORITE

The present invention relates to a process for the conversion of anthracenes to anthraquinones.

Anthraquinone has been used in the manufacture of dyestuff. Recently, however, anthraquinones have been discovered to be particularly useful for improving the yield and quality of pulp in commercial wood pulping processing. In view of the vast quantities required for this large scale industrial use, a need developed for a simple, nontoxic and cost effective process for manufacturing large scale quantities of anthraquinone.

Anthraquinones have been manufactured by a variety of different processes, all directed to provide extremely high yield and great purity of product. Various organic liquid phase oxidation reactions are known to produce anthraquinone from anthracene. See for example U.S. Pat. No. 2,821,534 which utilizes nitric acid as an oxidizing agent and U.S. Pat. No. 3,541,115 which teaches the use of gaseous chlorine to oxidize anthracene at high reaction temperatures. The need for an alternative oxidizing agent to the popular nitric acid was occasioned by the discovery that the nitric acid oxidized reaction of 2-methyl anthracene produces as a byproduct 2-methyl-1-nitro anthraquinone, which is now know as a mutagen and animal carcinogen.

In general the prior art processes to prepare anthraquinones are known to be expensive to operate. They frequently are not very cost effective to prepare anthraquinones in large volumes due to the high reaction temperature or pressure requirement and/or due to expensive oxidizing agents or initiators.

Sodium hypochlorite is a known oxidizing agent. For example, U.S. Pat. No. 2,821,534 suggest the use of sodium hypochlorite as an oxidizing agent in an organic liquid phase oxidation reaction. However, sodium hypochlorite when used as an oxidizing agent has commonly been found to be most effective in highly basic environments. See for example U.S. Pat. No. 3,291,825 which suggest a pH of above 13 to oxidize phenanthracene to diphenic acid.

The use of sodium hypochlorite to oxidize anthracene is specifically discouraged in the literature. Frank R. Mayo in Fuel, Vol. 54, pages 273-275, October, 1974, discloses that various experiments show anthracene was inert at reaction temperatures of 60°-70° C. at an apparently high pH.

It has now been discovered that anthracenes dissolved in an inert organic solvent may be inexpensively oxidized to anthraquinones by the utilization of sodium hypochlorite as the oxidizing agent, provided the reaction is allowed to proceed at a pH of less than about 8.

The solvent should be chosen preferably for its non-reactivity under the conditions of the reaction, its ability to increase the reaction rate as a medium of the reaction without change of chemical composition, its relatively higher solubility for anthracene as compared to anthraquinone at the temperature of the reaction, its boiling point for ease in removal of the liquid-diluent as a constituent of the boiling mixture and in further recovery during subsequent separation operations.

Preferably such a solvent is a liquid hydrocarbon or a halogenated hydrocarbon. Practically all liquid halogenated hydrocarbons are solvents for anthracenes. Therefore, solvents such as chloroform, carbon tetrachloride, dichlorobenzene and trichlorobenzene, tetrachloroethylene, methylene chloride, xylene and trichloroethylene and the like may be employed. Other non-halogenated solvents such as nitrobenzene, and toluene may also be employed. It should be noted that the nature or character of the solvent-diluent is not critical as long as it is an inert organic solvent for the anthracene. For purposes of practical expediency it is suggested to use tetrachloroethylene.

Useful anthracenes which may be used as starting compounds in the present invention include anthracene, 2-methyl anthracene, 9-chloro anthracene, 9, 10-dihydroanthracene and other substituted anthracenes.

The sodium hypochlorite may be used in aqueous solutions of 0.5 to 15% by weight and should be present in a mole ratio to the anthracene of from at least 3:1 to about 7:1 moles. Preferably, however, for best results the aqueous solution should contain an amount of sodium hypochlorite of from about 10 to 15% by weight.

As indicated herein above the pH range of the reaction should be from about 4.5 to about 8. Operating the process at a pH below 4.5 causes detrimental side reactions and running the process above a pH of about 8.0 provides for a very slow rate of reaction as well as undesirable byproducts. A preferred pH range to obtain optimum results is from about 5.5 to 8.

The total reaction pressure of the system, particularly the reaction zone, is preferred to be atmospheric for general ease of operation and simplicity of equipment. However, higher or lower pressures may be used depending on the choice of solvent-diluent.

The reaction temperatures do not appear to be critical and the reaction may be performed conveniently at room temperature.

The following examples illustrate the present invention.

EXAMPLE 1

A vessel was charged with 4.81 grams of 2-methylanthracene which is 96.7% pure, 50 milliliters of distilled tetrachloroethylene, and 173 grams of a sodium hypochlorite aqueous solution containing 8.04 grams of sodium hypochlorite, providing for a mole ratio of sodium hypochlorite to anthracene of 4.34:1. 4.5 Milliliters of concentrated hydrochloric acid were added to the stirred mixture to adjust the pH to about 7. During the resulting reaction about 12 milliliters of 3 N sodium hydroxide was added to maintain the pH at about 7. Reaction temperature was about 30° C. After about three hours the aqueous layer was removed and the organic layer was found to contain 95% of 2-methylanthraquinone.

The following experiments 2 through 18 compared the effect of pH of the reaction.

EXAMPLE 2-18

4.81 Grams of 2-methylanthracene (MAC) (25m moles) (96.7% pure) were dissolved in 50 milliliters of tetrachloroethylene and stirred. 140.5 grams of 5.3% aqueous sodium hypochlorite was added. The mole ratio of sodium hypochlorite to MAC was 4.34:1 mole. Concentrated hydrochloric acid was added to reach the desired pH point and the mixture was stirred for three hours. Samples of both phases were removed periodically for analysis. The pH was controlled within a ±0.1 pH unit. In response to observing pH changes, adjustments were made to maintain the desired pH by adding 3 Normal sodium hydroxide from a syringe into the upper level of the stirred mix. The results of the experiments 2 through 18 obtained by gas liquid chromatography analysis are indicated in Table I.

TABLE I

Effect of pH Control Method

| Experiment # | Control pH | % MAC | % MAQ | % Cl-MAC | % Cl$_2$MAC |
|---|---|---|---|---|---|
| 2 | 5 | — | 92.1 | 0.2 | 0.33 |
| 3 | 5.4 | 0 | 92.5 | 0.5 | 0.9 |
| 4 | 5.6 | — | 100 | — | — |
| 5 | 5.8 | 0.3 | 91.7 | 2.4 | 1.4 |
| 6 | 6 | 0.45 | 94.6 | 1.0 | 0.97 |
| 7 | 6.2 | 0.37 | 97.0 | 0.25 | 0.8 |
| 8 | 6.4 | 0.72 | 93.8 | 2.8 | 1.1 |
| 9 | 6.6 | 0.32 | 95.68 | 1.31 | 1.05 |
| 10 | 6.8 | 0.8 | 95.3 | 2.18 | 0.4 |
| 11 | 7.0 | 0.74 | 93.82 | 1.73 | 2.18 |
| 12 | 7.2 | 1.17 | 95.1 | 2.3 | 1.44 |
| 13 | 7.4 | 3.92 | 94.40 | 1.90 | 0 |
| 14 | 7.6 | 0.1 | 95.7 | 2.9 | 0 |
| 15 | 7.8 | 2.4 | 92.3 | 3.2 | 1.1 |
| 16 | 8.0 | 0.19 | 99.45 | 0.36 | 0 |
| 17 | 8.5 | 5.57 | 80.35 | 8.13 | 0 |
| 18 | 9.0 | 43.36 | 36.70 | 9.70 | 0.5 |

What is claimed is:

1. A method for the preparation of anthraquinones which comprises oxidizing corresponding anthracenes dissolved in an inert organic solvent in the presence of an aqueous solution of sodium hypochlorite as oxidizing agent and maintaining the pH of the process at from about 4.5 to about 8.0.

2. A method according to claim 1 wherein the anthracene is 2-methyl anthracene and the solvent is tetrachloroethylene.

3. A method according to claim 1 wherein the pH is from about 5.5 to 8.0.

4. A method according to claim 1 wherein the sodium hypochlorite solution contains from about 0.5 to 15% by weight of sodium hypochlorite.

5. A method according to claim 4 wherein the sodium hypochlorite solution contains from about 10 to 15% by weight of sodium hypochlorite.

6. A method according to claim 1 wherein the mole ratio of sodium hypochlorite to the anthracene is from about 3:1 to 7:1.

7. A method according to claim 6 wherein the mole ratio of sodium hypochlorite to the anthracene is from about 4:1 to 6:1.

* * * * *